US012324646B2

United States Patent
Li et al.

(10) Patent No.: US 12,324,646 B2
(45) Date of Patent: Jun. 10, 2025

(54) DEFLECTION DETECTOR, METHOD OF CONTROLLING DEFLECTION DETECTOR, ELECTRIC STAPLER, AND MEDICAL DEVICE

(71) Applicant: Surgnova Healthcare Technologies (Zhejiang) Co., Ltd., Cixi (CN)

(72) Inventors: Guangrong Li, Cixi (CN); Yang Li, Cixi (CN); Guoyu Zhang, Cixi (CN)

(73) Assignee: Surgnova Healthcare Technologies (Zhejiang) Co., Ltd., Cixi (CN)

( * ) Notice: Subject to any disclaimer, the term of this patent is extended or adjusted under 35 U.S.C. 154(b) by 0 days.

(21) Appl. No.: 18/695,161

(22) PCT Filed: Jul. 29, 2022

(86) PCT No.: PCT/CN2022/109114
§ 371 (c)(1),
(2) Date: Mar. 25, 2024

(87) PCT Pub. No.: WO2023/045562
PCT Pub. Date: Mar. 30, 2023

(65) Prior Publication Data
US 2024/0390091 A1   Nov. 28, 2024

(30) Foreign Application Priority Data
Sep. 26, 2021 (CN) .......................... 202111146884.8

(51) Int. Cl.
*A61B 17/072* (2006.01)
*A61B 34/00* (2016.01)
*A61B 17/00* (2006.01)

(52) U.S. Cl.
CPC ........ *A61B 34/74* (2016.02); *A61B 17/07207* (2013.01); *A61B 2017/00398* (2013.01)

(58) Field of Classification Search
CPC ..................................................... A61B 34/74
See application file for complete search history.

(56) References Cited

U.S. PATENT DOCUMENTS

| 4,503,842 A | 3/1985 | Takayama |
| 2007/0185486 A1 | 8/2007 | Hauck et al. |

(Continued)

FOREIGN PATENT DOCUMENTS

| CN | 200980692 Y | 11/2007 |
| CN | 101569550 A | 11/2009 |

(Continued)

OTHER PUBLICATIONS

International Search Report and Written Opinion for PCT Application No. PCT/CN2022/109114, Dated Oct. 28. 2022, 12 pages including English Translation.

(Continued)

*Primary Examiner* — Nathaniel C Chukwurah
(74) *Attorney, Agent, or Firm* — Christopher R. Christenson; Kelly, Holt & Christenson, P.L.L.C.

(57) ABSTRACT

A deflection detector and a control method thereof, an electric stapler, and a medical device. The deflection detector is applied to a detection on a deflection action of an operating end of a medical device, including: a driving portion, used to perform a rotation action to provide a driving force for achieving the deflection action of the operating end; an interface portion, in transmission connection with the driving portion and used to convert the rotation action of the driving portion into a linear movement action along an axial direction; and a detecting portion, on the interface portion and used to detect a movement position of the linear movement action of the interface portion along the axial direction relative to a supporting portion, so as to complete the detection on the deflection action.

14 Claims, 8 Drawing Sheets

(56) References Cited

U.S. PATENT DOCUMENTS

2009/0090763 A1\* 4/2009 Zemlok ............ A61B 17/07207
  227/175.2
2011/0015569 A1   1/2011 Kirschenman et al.
2013/0226155 A1   8/2013 Bookbinder et al.

FOREIGN PATENT DOCUMENTS

| | | |
|---|---|---|
| CN | 104135952 A | 11/2014 |
| CN | 104783844 A | 7/2015 |
| CN | 106491211 A | 3/2017 |
| CN | 111761609 A | 10/2020 |
| CN | 211723295 U | 10/2020 |
| CN | 111904515 A | 11/2020 |
| CN | 111973243 A | 11/2020 |
| CN | 212699005 U | 3/2021 |
| CN | 112617937 A | 4/2021 |
| CN | 113842181 A | 12/2021 |
| CN | 114901165 A | 8/2022 |
| WO | 2019116274 A1 | 6/2019 |

OTHER PUBLICATIONS

First Office Action for Chinese Application No. 202111146884.8, Dated Apr. 5, 2023, 17 pages including English Translation.

\* cited by examiner

DEFLECTION DETECTOR, METHOD OF CONTROLLING DEFLECTION DETECTOR, ELECTRIC STAPLER, AND MEDICAL DEVICE

CROSS REFERENCE TO RELATED APPLICATION(S)

This application is a Section 371 National Stage Application of International Application No. PCT/CN2022/109114, filed on Jul. 29, 2022, which claims priority to Chinese Patent Application No. 202111146884.8, filed on Sep. 26, 2021 and entitled "DEFLECTION DETECTOR, METHOD OF CONTROLLING DEFLECTION DETECTOR, ELECTRIC STAPLER, AND MEDICAL DEVICE", the entire content of which is incorporated herein in its entirety by reference.

TECHNICAL FIELD

The present disclosure relates to a field of medical device technology, and in particular to a deflection detector, a method of controlling a deflection detector, an electric stapler, and a medical device.

BACKGROUND

A jaw component at a front end of an existing electric stapler is required to be able to deflect after entering the human body, so that a staple cartridge may contact lesions at different positions and angles to complete a surgery. However, due to a limited operating space and limited field of view in the human body, there may be collisions with internal tissues and organs or discontinuous deflection angles during the deflection process, leading to the inability to reach the lesion location. As a result, in mild cases, the surgery cannot be effectively completed, while in severe cases, it may cause organ damage and expand the surgical scope. Moreover, there is a maximum angle limitation on the deflection of the jaw component at the front end of the existing electric stapler. However, due to the precision of the mechanical structure, it is difficult to effectively provide a limit mechanism, which makes it easy for the jaw component of the stapler to deflect beyond the maximum usage angle, resulting in insufficient cutting or stapling energy, even the breakage of the cutting blade, expanding the surgical range, and causing serious secondary injury to patients.

SUMMARY

An aspect of the present disclosure provides a deflection detector, applied to a detection on a deflection action of an operating end of a medical device, including a driving portion, an interface portion and a detecting portion. The driving portion is used to perform a rotation action to provide a driving force for achieving the deflection action of the operating end; the interface portion is in transmission connection with the driving portion and used to convert the rotation action of the driving portion into a linear movement action along an axial direction; and the detecting portion is provided on the interface portion and used to detect a movement position of the linear movement action of the interface portion along the axial direction relative to a supporting portion, so as to complete the detection on the deflection action.

According to an embodiment of the present disclosure, the deflection detector further includes the supporting portion used to support the deflection detector, wherein the driving portion is provided on the supporting portion.

According to an embodiment of the present disclosure, the supporting portion includes a supporting frame, a rotating head and a rotating housing. The supporting frame is a frame structure with a hollow space and serves as a supporting main body of the supporting portion; the rotating head is a cylindrical structure, is provided at an end of the supporting frame facing the operating end, and serves as a contact end between the supporting portion and the interface portion; and the rotating housing covers the rotating head and the interface portion and is used to rotate relative to the supporting frame, wherein an opening of the rotating housing is matched with an outer-ring surface of the cylindrical structure of the rotating head.

According to an embodiment of the present disclosure, the driving portion includes a switching component and a motor component. The switching component is opposite to the rotating housing, is provided on the supporting frame, and serves as a driving switch for the driving portion when the switching component is in contact with the rotating housing; and the motor component is electrically connected to the switching component, provided in an accommodating space of the supporting frame, and used to provide the driving force in response to a driving switch action of the switching component, so as to provide the rotation action to the interface portion.

According to an embodiment of the present disclosure, the switching component includes a switching element and a circuit board. The switching element is arranged opposite to the opening of the rotating housing and serves as a contact element of the driving switch; and the circuit board is provided on a side of the switching element, embedded on the supporting frame, electrically connected to the motor component, and used to generate an electrical signal for controlling a motor rotation direction of the motor component.

According to an embodiment of the present disclosure, the rotating housing includes a semi-ring convex portion provided on the rotating housing along an outer edge of the opening of the rotating housing and opposite to the switching element, wherein two end portions of the semi-ring convex portion have sloping surfaces, wherein when the rotating housing rotates relative to the supporting frame and the sloping surface of the end portion of the semi-ring convex portion is in contact with the switching element, the switching element triggers an electrical contact on the circuit board to generate the electrical signal for controlling the motor rotation direction of the motor component.

According to an embodiment of the present disclosure, the motor component includes a motor unit and a gear unit. The motor unit has an output motor and is used to control the output motor to rotate according to the electrical signal for the motor rotation direction, so as to provide the driving force; and the gear unit is in transmission connection with the motor unit and used to convert the driving force into the rotation action.

According to an embodiment of the present disclosure, the interface portion includes an interface seat and a transmitter. The interface seat is in transmission connection with a gear unit of the motor component and used to convert the rotation action of the driving portion into the linear movement action along the axial direction; and the transmitter has an end connected to the interface seat and the other end connected to the operating end, wherein the transmitter is used to convert the linear movement action of the interface seat into the deflection action of the operating end.

According to an embodiment of the present disclosure, the detecting portion includes a thimble component provided in a fixed hole of the interface seat and used to detect the movement position of the linear movement action of the interface portion along the axial direction relative to the supporting portion.

According to an embodiment of the present disclosure, the thimble component includes a plurality of thimbles, a thimble sleeve, and a fixed sleeve. The plurality of thimbles are in contact with electrical contacts of the supporting portion, wherein different detection signals are formed in response to electrical contacts at different positions being detected, and the movement position is fed back using the detection signal; the thimble sleeve is sheathed the plurality of thimbles, and used to provide attachment positions for the plurality of thimbles; and the fixed sleeve is sheathed the thimble sleeve, provided in the fixed hole of the interface seat, matched with the fixed hole, and used to fix the thimble sleeve sheathed the plurality of thimbles in the fixed hole.

According to an embodiment of the present disclosure, the supporting portion further includes a limiting plate provided on an edge of an end surface of the rotating head facing the interface portion and corresponding to the fixed hole of the interface seat, wherein a rear end electrical contact group, a zero position electrical contact group, and a front end electrical contact group are provided on a surface of the limiting plate facing the interface seat, and movement position detections on a rear end position, a zero position, and a front end position of the interface portion relative to the supporting portion are achieved when the rear end electrical contact group, the zero position electrical contact group, and the front end electrical contact group are respectively in contact with the plurality of thimbles of the thimble component.

Another aspect of the present disclosure provides a method of controlling the above-described deflection detector, including: providing, by the driving portion of the deflection detector, the driving force for achieving the deflection action of the operating end, in response to a detection instruction; converting, using the interface portion of the deflection detector, the rotation action of the driving portion into the linear movement action along the axial direction; and controlling the detecting portion of the deflection detector to detect the movement position of the linear movement action of the interface portion along the axial direction relative to the supporting portion, so as to complete the detection on the deflection action.

Another aspect of the present disclosure provides an electric stapler, including the above-described deflection detector and a jaw component, the above-described deflection detector is used to detect the movement position of the linear movement action of the interface portion along the axial direction relative to the supporting portion; and the jaw component is in transmission connection with the interface portion of the deflection detector and serves as the operating end to perform the deflection action according to the detection on the movement position.

Another aspect of the present disclosure provides a medical device including the deflection detector described above.

DETAILED DESCRIPTION OF EMBODIMENTS

Figure 1:
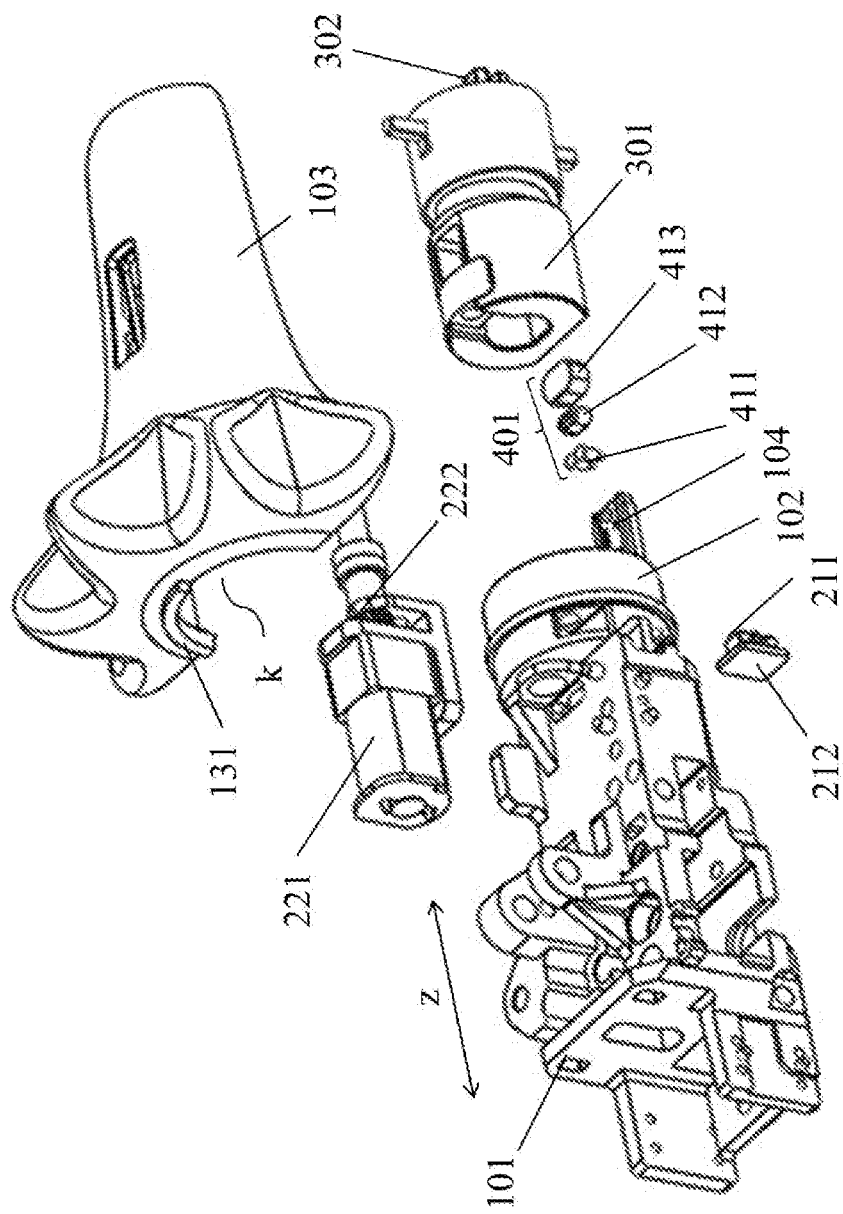
FIG. 1 schematically shows a three-dimensional explosion diagram of a deflection detector from a perspective according to an embodiment of the present disclosure.

In order to make the purposes, technical solutions, and advantages of the present disclosure clearer, the present disclosure is further explained in detail combining specific embodiments and referring to accompanying drawings.

It should be noted that the implementation methods not shown or described in the accompanying drawings or the specification are all in forms known to those ordinary skilled in the art, which are not explained in detail. In addition, the above definitions of each element and method are not limited to the various specific structures, shapes, or methods described in embodiments, which may be simply modified or replaced by those ordinary skilled in the art.

It should also be noted that the directional terms described in embodiments, such as "up", "down", "front", "back", "left", "right", etc., are only for reference to the direction of the drawings and are not intended to limit the scope of the protection of the present disclosure. Throughout the drawings, the same elements are represented by the same or similar reference numbers. Existing structures or constructions will be omitted when they may cause confusion in the understanding of the present disclosure.

In addition, the shape and size of each component in the drawings do not reflect the real size and proportion, but only represent the content of embodiments of the present disclosure. Furthermore, in the claims, any reference symbol located between parentheses should not be constructed as a limitation on the claims.

Furthermore, the word "including" does not exclude the presence of elements or steps not listed in the claims. The word "one" or "a" before an element does not exclude the existence of a plurality of such elements.

The use of ordinal numbers such as "first", "second", "third", etc. in the specification and claims for describing the corresponding elements does not imply that the element has any ordinal numbers, nor does it represent the order of one element and another element or the order of the manufacturing method. The use of these ordinal numbers is only to enable an element with a certain name to be clearly distinguished from another element with the same name.

Those skilled in the art may understand that the modules in the devices in embodiments may be adaptively changed and provided in one or more devices different from embodiments. The modules, units, or components in embodiments may be combined into one module, unit, or component. In addition, the modules, units, or components in embodiments may be divided into a plurality of sub-modules, sub-units, or sub-components. Except for at least some of such features and/or processes or units that are mutually exclusive, any combination may be used to combine all features disclosed in the specification (including accompanying claims, abstracts, and drawings), as well as all processes or units of any method or device thus disclosed. Unless otherwise explicitly stated, each feature disclosed in the specification (including accompanying claims, abstracts, and drawings) may be replaced by alternative features that provide the same, equivalent, or similar purposes. Moreover, in the unit claims listing several devices, several of these devices may be specifically embodied through the same hardware item.

Similarly, it should be understood that in order to streamline the present disclosure and assist in understanding one or more aspects of the present disclosure, in the description of exemplary embodiments of the present disclosure above, the various features of the present disclosure are sometimes grouped together into a single embodiment, figure, or description thereof. However, the disclosed method should not be interpreted as reflecting the intention that the claimed protection of the present disclosure has more features than those explicitly recorded in each claim. More precisely, as reflected in the following claims, the disclosure aspects are less than all features of the previously disclosed single embodiment. Therefore, the claims that follow the specific implementation method are explicitly incorporated into the specific implementation method, where each claim itself serves as a separate embodiment of the present disclosure.

At present, electric staplers in the related art are mainly divided into two types: the semi-automatic stapler and the fully automatic stapler, which provide different solutions for the deflection problem of electric staplers respectively. The deflection action may be completed with defects, but there are certain risks during surgery.

The semi-automatic stapler (which may achieve closing manually, deflecting manually, and firing electrically), as well as some fully automatic staplers without sensors, all use manual methods to deflect the staple cartridge and the seat of the staple cartridge. By equipped with knobs, continuous angle rotation may be achieved. However, when rotating, the front end needs to be pressed against a fixed position, which may be completed with both hands. The operator may easily perform the rotation operation by using a position in a body as the fixed position, which is inconvenient to operate and may cause danger. In addition, the fully automatic stapler uses a motor to drive the deflection of the staple cartridge and the seat of the staple cartridge, which mostly cannot be operated with one hand, and some cannot achieve continuous angle. There is also a problem of unclear button definition, that is, due to issues for the rotation angle, the same button may cause the staple cartridge and the seat of the staple cartridge to deflect to the left in some cases, and also to deflect to the right in other cases, which is prone to operation errors.

Moreover, the existing staplers mostly use mechanical limits when deflecting to the maximum angle limit. When the deflection angle reaches the limit of use, the mechanical structure is used to prevent further deflection. If the doctor continues to exert force or press the motor, the former may damage the limit and damage the instrument, while the latter may cause the motor to be locked-rotor, consume battery power, and result in insufficient cutting energy. If the locked-rotor motor current is too large, it may also cause serious accidents such as heat damage. Note that the laparoscopic stapler is a high-precision handheld device with limited instrument space, which means that existing staplers do not have the function of detecting the deflection direction and the deflection direction may only be determined visually by doctors.

To solve at least one of the technical problems in the deflection process of the jaw component of the electric stapler in the related art, the present disclosure provides a deflection detector, a method of controlling a deflection detector, an electric stapler, and a medical device to add the function of detecting the deflection direction in a narrow precision mechanical space, thereby adding the electronic limit detection on the premise of having mechanical limits. The design is stable, reliable, and cost-effective.

As shown in FIGS. 1 to 8, an aspect of the present disclosure provides a deflection detector, applied to a detection on a deflection action of an operating end of a medical device, including a driving portion, an interface portion, and a detecting portion.

The driving portion is used to perform a rotation action to provide a driving force for achieving the deflection action of the operating end.

Then interface portion is in transmission connection with the driving portion and used to convert the rotation action of the driving portion into a linear movement action along an axial direction.

The detecting portion is provided on the interface portion and used to detect a movement position of the linear movement action of the interface portion along the axial direction relative to a supporting portion, so as to complete the detection on the deflection action.

The driving portion is a power structure of the deflection detector, which is used to output the driving force. For example, the driving portion may perform the rotation action through forms such as motor output, and provide the driving force to the deflection action of the operating end through the output conversion of the rotation action.

The interface portion is a connection structure between the driving portion and the operating end, achieving a transmission connection with the driving portion. The so-called transmission connection refers to that the interface portion may perform a linear movement action along the axial direction relative to the driving portion when the interface portion is connected to the driving portion, achieving the transmission of the driving portion to the interface portion, so that the interface portion drives the operating end to perform the deflection action. Specifically, the interface portion may convert the rotation action provided by the driving portion into the linear movement action along the axial direction through structural limit design. The interface portion, as an intermediate structure of the transmission connection, may play a corresponding limiting role to limit the distance of the transmission connection, so that the deflection action may not exceed the set deflection angle.

The detecting portion is located on the main structure of the interface portion and may directly detect the movement position of the interface portion relative to the supporting portion in the linear movement process of the interface portion along the axial direction relative to the supporting portion. As the linear movement action of the interface portion along the axial direction z may be converted by the operating end to perform the deflection action, the movement position obtained by the detecting portion may be used to feedback on the execution status of the deflection action, such as a deflection direction, a deflection angle, and the like.

Therefore, an electronic limit position detection may be added on the premise of having mechanical limits, so that the operating end (such as the jaw component) may stop deflecting before hitting the mechanical limit portion when performing the deflection operation, thereby effectively preventing the deflection impact. In addition, the deflection process does not require manual force, the deflection direction is stable which is not limited by the position of the jaw, and continuous angle rotation may be achieved. The deflection direction and angle meet the doctor's expectations, and fully single handed operation may be achieved.

As shown in FIGS. 1 to 8, according to an embodiment of the present disclosure, the deflection detector further includes the supporting portion used to support the deflection detector, and the driving portion is provided on the supporting portion.

The supporting portion is used to provide the main body support for the deflection detector, so that the driving portion, the interface portion, and the detecting portion may be attached to the supporting portion, thereby improving the structural integration and mechanical precision of the deflection detector and reducing the volume of the deflection detector, which is more conducive to achieving single handed operation by users.

As shown in FIGS. 1 to 8, according to an embodiment of the present disclosure, the supporting portion includes a supporting frame 101, a rotating head 102, and a rotating housing 103.

The supporting frame 101 is a frame structure with a hollow space and serves as a supporting main body of the supporting portion.

The rotating head 102 is a cylindrical structure and provided at an end of the supporting frame 101 facing the operating end, and serves as a contact end between the supporting portion and the interface portion.

The rotating housing 103 covers the rotating head 102 and the interface portion and used to rotate relative to the supporting frame 101, and an opening k of the rotating housing 103 is matched with an outer-ring surface of the cylindrical structure of the rotating head 102. The rotating housing 103 is usually a combination of two symmetrical shell structures. FIG. 1 only shows half of the shell structure, which is half of the rotating housing 103.

The supporting frame 101 is the main structure of the supporting portion, which is a supporting skeleton with a hollow space and a plurality of different setting positions. The driving portion, the interface portion, and the detecting portion may be attached to the supporting skeleton and provided at different setting positions to achieve structural integration of the supporting skeleton.

The rotating head 102, as the end head of the supporting frame 101, is provided to face the interface portion. The outer surface of the rotating head 102 is a smooth cylindrical surface (i.e. the outer-ring surface). The size of the opening k of the rotating housing 103 may be matched with the size of the cylindrical surface. After completing the cooperated providing of the rotating housing 103 and the rotating head 102, the rotating housing 103 may rotate relative to the rotating head 102, achieving the rotation of the rotating housing 103 relative to the supporting frame 101 of the supporting portion.

The opening k of the rotating housing 103 and the rear edge of the rotating head 102 facing the supporting frame 101 are cooperated provided. The two symmetrical sub-shells of the rotating housing 103 are cooperated with each other to cover the main bodies of the interface portion and the rotating head 102, so that the rotating housing 103 may both protect and isolate the deflection detector.

As shown in FIGS. 1 to 8, according to an embodiment of the present disclosure, the driving portion includes a switching component and a motor component.

The switching component is opposite to the rotating housing 103, provided on the supporting frame 101, and serves as a driving switch for the driving portion when the switching component is in contact with the rotating housing 103.

The motor component is electrically connected to the switching component, provided in an accommodating space of the supporting frame 101, and used to provide the driving force in response to a driving switch action of the switching component, so as to provide the rotation action to the interface portion.

After the power supply of the deflection detector is switched on, the driving switch of the driving portion is achieved through the switching component. Specifically, the rotating housing 103 may be in contact with the switching component and trigger the driving switch by rotating the rotating housing 103, so that the switching component generates a circuit current signal that controls the motor rotation direction of the motor component via triggering.

The motor component may drive and rotate the motor in response to the circuit current signal, as well as provide the driving force output to perform the rotation action output. Therefore, the driving portion is mainly used to provide the power for the deflection operation in response to the deflection operation trigger. The driving portion serves as the main power source for the deflection detector.

As shown in FIGS. 1 to 8, according to an embodiment of the present disclosure, the switching component includes a switching element 211 and a circuit board 212.

The switching element 211 is arranged opposite to the opening k of the rotating housing 103 and serves as a contact element of the driving switch.

The circuit board 212 is provided on a side of the switching element 211, embedded on the supporting frame 101, electrically connected to the motor component, and used to generate an electrical signal for controlling a motor rotation direction of the motor component.

The switching element 211 is provided on the circuit board 212 through a fixed element. The switching element 211 is sheathed in the fixed element, and may enter or exit the fixed element relative to the surface of the fixed element. Specifically, elastic elements such as a spring may be provided in the fixed element, so that when the switching element 211 is compressed by the external force, the switching element 211 may compress the elastic element and enter the fixed element. When the external force is released, the switching element 211 may undergo elastic recovery by the elastic force of the elastic element and exit the fixed element.

The fixed element may be fixed on the circuit board 212 through methods such as welding.

The circuit board 212 is electrically connected to the switching element 211. The circuit board 212 may generate an electrical signal due to the entry or exit of the switching element 211 from the fixed element, and the electrical signal is transmitted to the motor component of the driving portion, so that the motor component of the driving portion drives and rotates the motor in a specific rotation direction in response to the electrical signal, as well as provides the driving force output to perform the rotation action output. The specific size of the circuit board 212 may be only 7 mm*5 mm. The circuit board 212 is installed on the central skeleton of the supporting frame 101 in a fastening manner, which has a reliable structural design, so that the circuit board 212 transmits the electrical signal through flexible circuits.

As shown in FIGS. 1 to 8, according to an embodiment of the present disclosure, the rotating housing 103 includes a semi-ring convex portion 131 provided on the rotating housing 103 along an outer edge of the opening k of the rotating housing 103 and opposite to the switching element 211, and two end portions of the semi-ring convex portion 131 have sloping surfaces. When the rotating housing 103 rotates relative to the supporting frame 101 and the sloping surface of the end portion of the semi-ring convex portion is in contact with the switching element 211, the switching element 211 triggers an electrical contact on the circuit board 212 to generate the electrical signal for controlling the motor rotation direction of the motor component.

Since the outer edge of the opening k of the rotating housing 103 is provided with a semi-ring convex structure as a semi-ring convex portion 131, the semi-ring convex portion 131 is protruded on the edge of the opening k and occupies half of the edge of the opening k. When the rotating housing 103 rotates, the semi-ring convex portion 131 may be in contact with the switching element 211 fixed on the circuit board 212 within a specific rotation range, and compress the switching element 211, so that the switching element 211 triggers the circuit board 212 to generate the above-described electrical signal.

The semi-ring convex portion 131 is not in contact with the switching element 211 within a rotation range of 0° to 180°. The switching element 211 may not trigger the circuit board 212 to generate the above-described electrical signal. On the contrary, the rotating housing 103 continues to rotate, and within the corresponding rotation range of 180° to 360°, the switching element 211 is in contact with the semi-ring convex portion 131. The semi-ring convex portion 131 compresses the switching element 211, so that the switching element 211 triggers the circuit board 212 to generate the above-described electrical signal. After the electrical signal is received by the driving portion, the motor may be controlled to rotate in a specific direction. In other words, the above-described electrical signal generated by the contact or detachment between the semi-ring convex portion 131 and the switching element 211 to control the motor rotation direction of the motor component may be used only to define the motor rotation direction, which is a rotation control electrical signal. For example, the electrical signal generated by the contact is used to define the clockwise rotation of the motor when it rotates, while the electrical signal generated by the detachment is used to define the counterclockwise rotation of the motor when it rotates. The rotation drive of the motor may be specifically achieved through the control circuit of other control buttons, that is, in the case of contact or detachment between the semi-ring convex portion 131 and the switching element 211, the motor may still be in a stationary state without receiving the control driving signal, and may not rotate to output the driving force.

In addition, in an embodiment of the present disclosure, a further electrical signal may be generated when there is no contact between the switching element 211 and the semi-ring convex portion 131 within the rotation range of 0° to 180° as described above. The further electrical signal may be of the same magnitude and opposite polarity as the electrical signal used to control the rotation of the motor of the motor component, so as to define the reverse rotation of the motor of the motor component. Therefore, under different contact conditions between the switching element 211 and the semi-ring convex portion 131, the electrical signals for different motor rotation directions define a forward rotation or reverse rotation of the motor component, and then the interface portion is driven to perform forward or backward linear movement along the axial direction z relative to the supporting portion when the motor rotates, achieving a change in the deflection direction of the operating end such as the jaw. The larger the distance of the linear movement, the greater the overall deflection angle of the front end.

Figure 6:
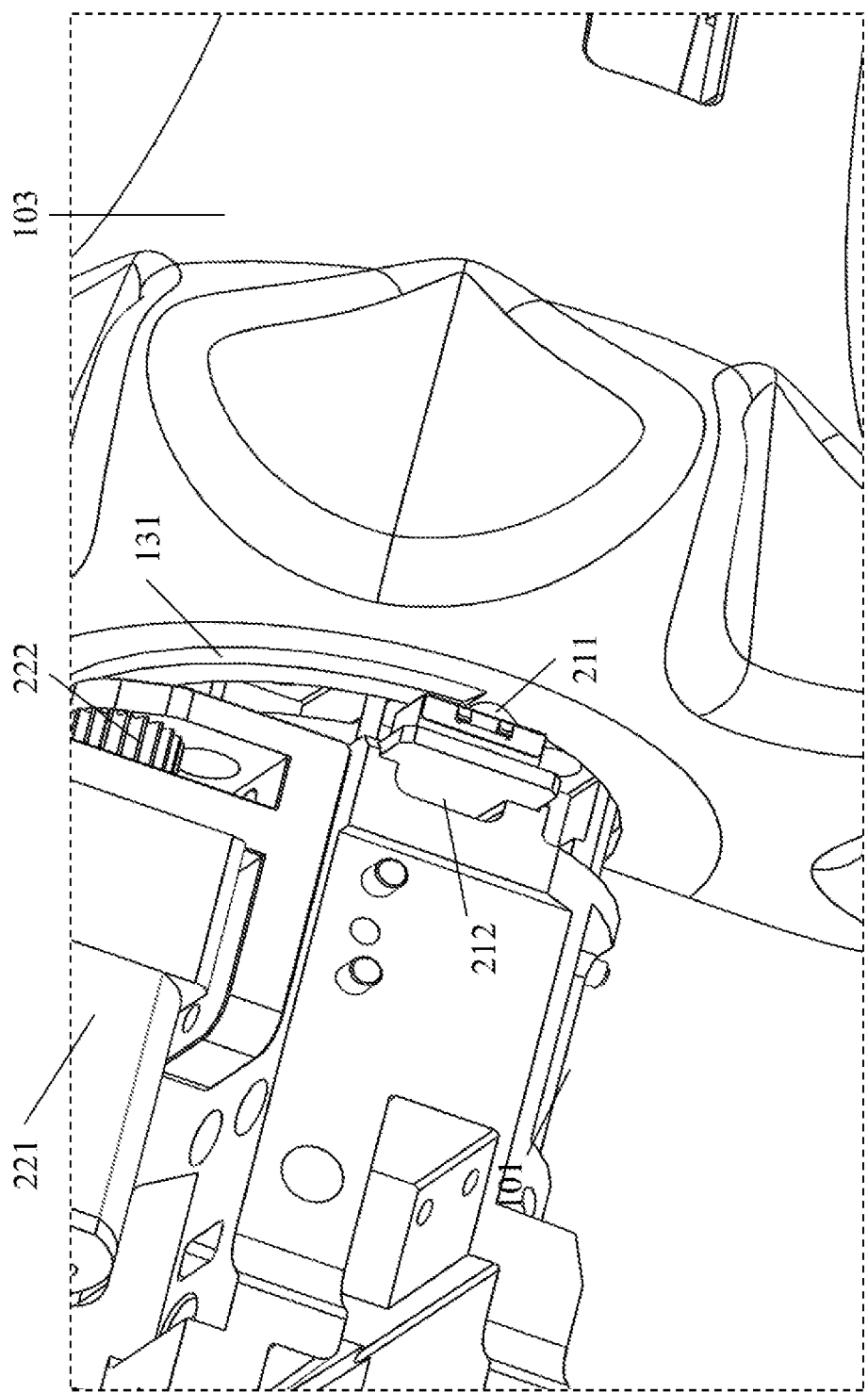
FIG. 6 schematically shows a local three-dimensional diagram of a rotating housing 103 of a deflection detector cooperating with a switching element 211 according to an embodiment of the present disclosure.
Figure 7:
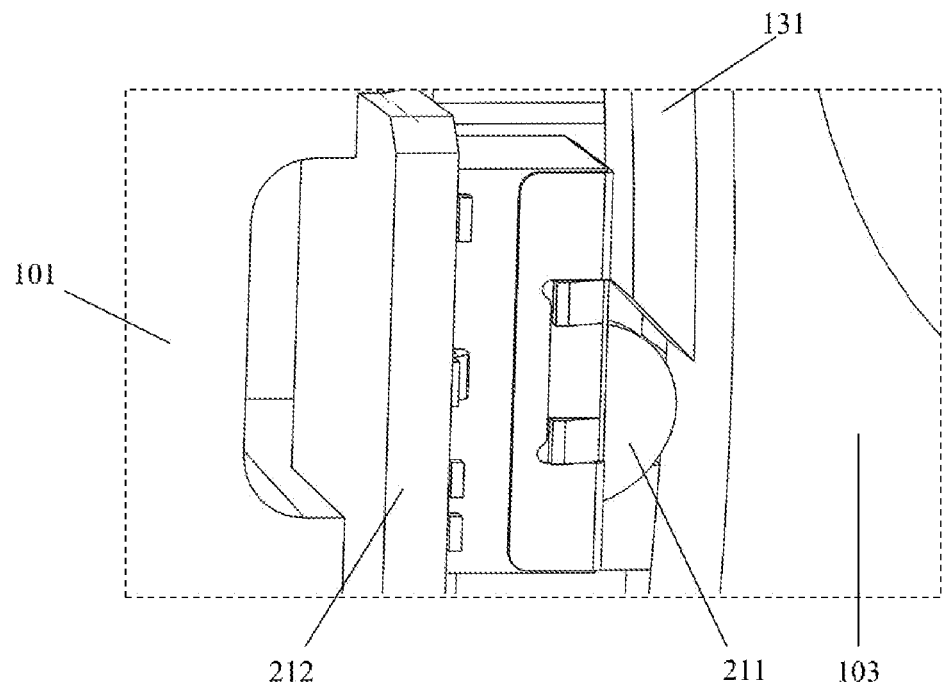
FIG. 7 schematically shows another local three-dimensional diagram of a rotating housing 103 of a deflection detector cooperating with a switching element 211 according to an embodiment of the present disclosure.
Figure 8:
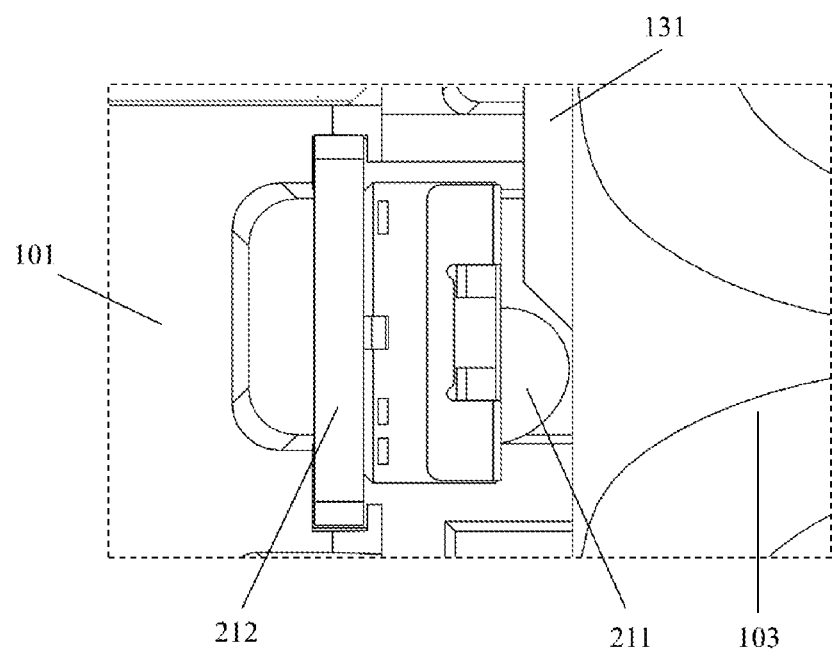
FIG. 8 schematically shows a local plan diagram (corresponding to FIG. 7) of a rotating housing 103 of a deflection detector cooperating with a switching element 211 according to an embodiment of the present disclosure.

It should be noted that, as shown in FIGS. 6 to 8, two end surfaces of the semi-ring convex portion 131 facing the switching element 211 are provided as inclined surfaces, so that when the semi-ring convex portion 131 rotates to the position of the switching element 211, the semi-ring convex portion 131 may be in buffered contact with the switching element 211 without collision, avoiding damage to the semi-ring convex portion 131 and the switching element 211. The outer surface of the corresponding switching element 211 in contact with the semi-ring convex portion 131 is provided as an arc-shaped outer surface, so that the inclined end surface and the contact plane of the semi-ring convex portion 131 are in contact with and presses the switching element 211 in a tangential direction, thereby better protecting the contact structure of the two and extending the service life of the switch while ensuring the contact effect.

The machining and assembly tolerances between the switching element 211 and the semi-ring convex portion 131 are included within the range of the switch triggering stroke, ensuring that the switch may be effectively triggered and may not be damaged.

As shown in FIGS. 1 to 8, according to an embodiment of the present disclosure, the motor component includes a motor unit 221 and a gear unit 222.

The motor unit 221 has an output motor and used to control the output motor to rotate according to the electrical signal for the motor rotation direction, so as to provide the driving force.

The gear unit 222 is in transmission connection with the motor unit 221 and used to convert the driving force into the rotation action.

Figure 3:
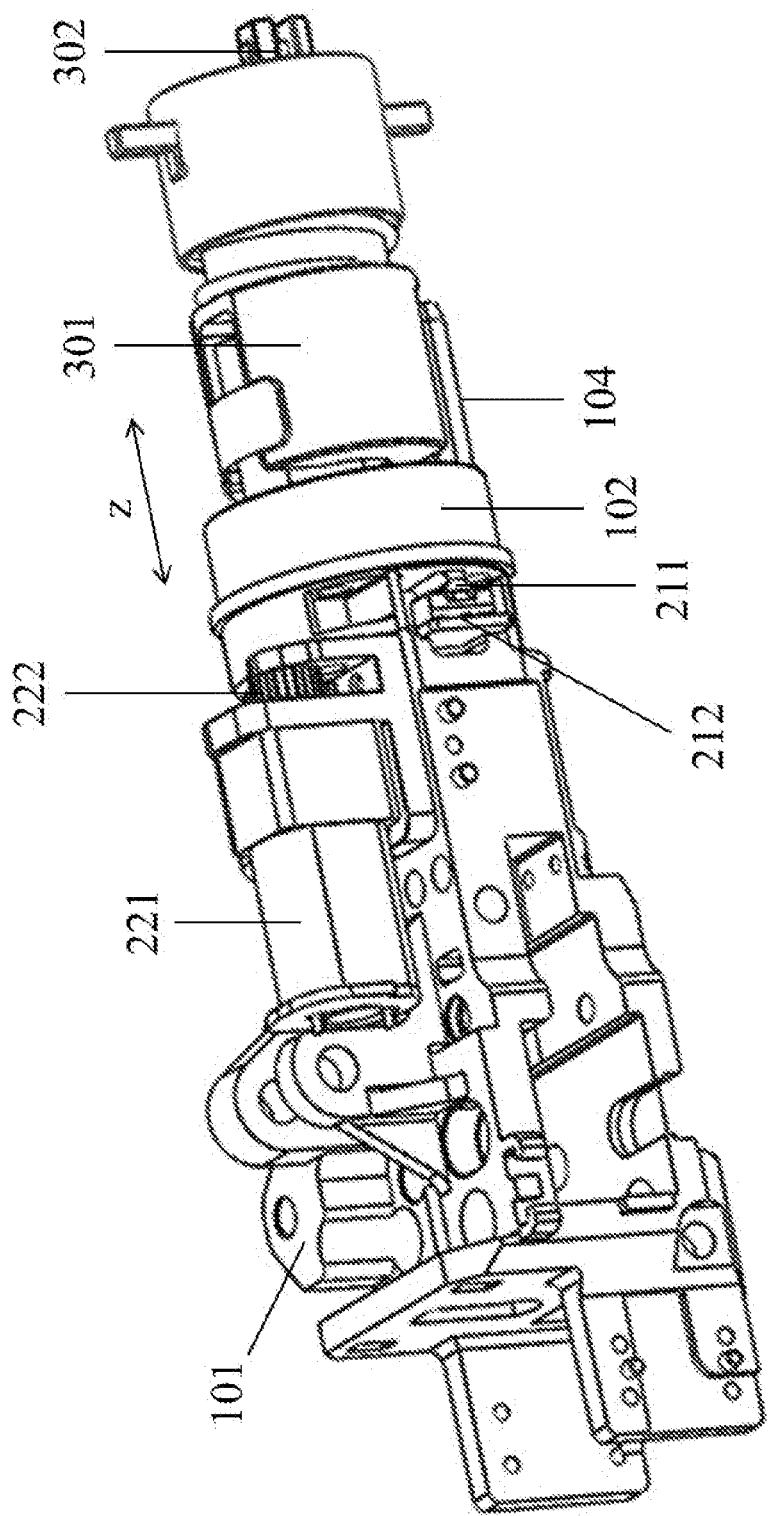
FIG. 3 schematically shows a three-dimensional composition diagram of a deflection detector from another perspective according to an embodiment of the present disclosure.
Figure 4:
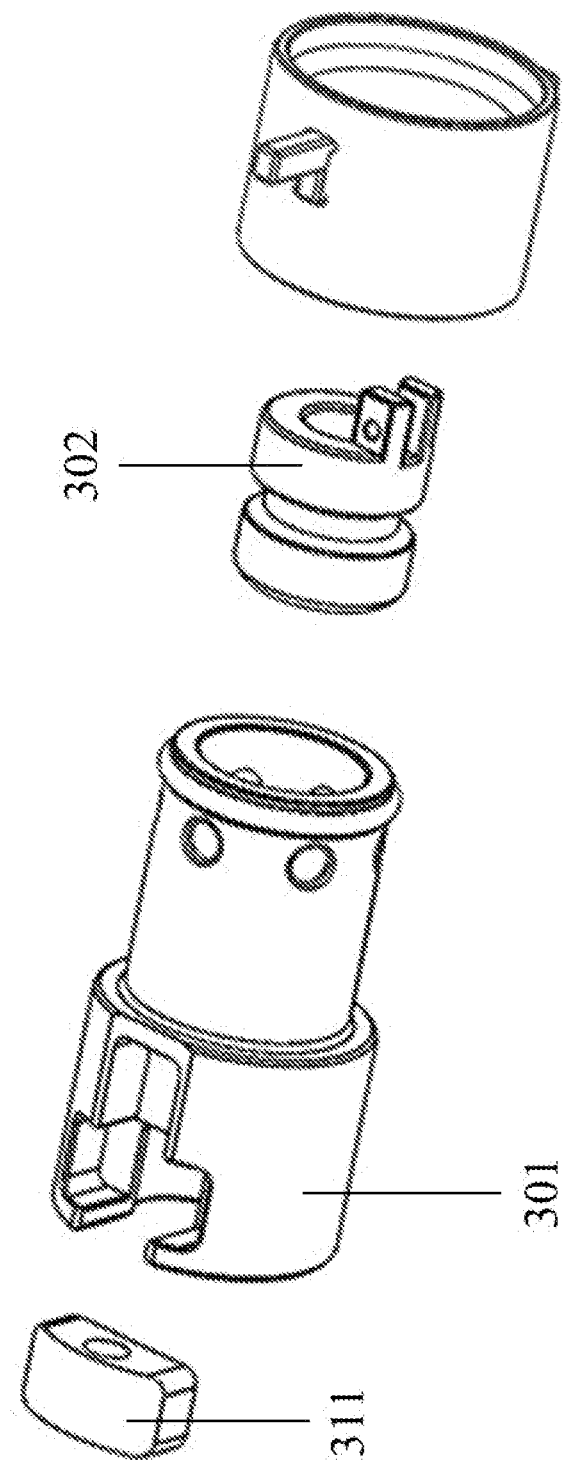
FIG. 4 schematically shows a three-dimensional composition diagram of an interface portion of a deflection detector from another perspective according to an embodiment of the present disclosure.
Figure 5:
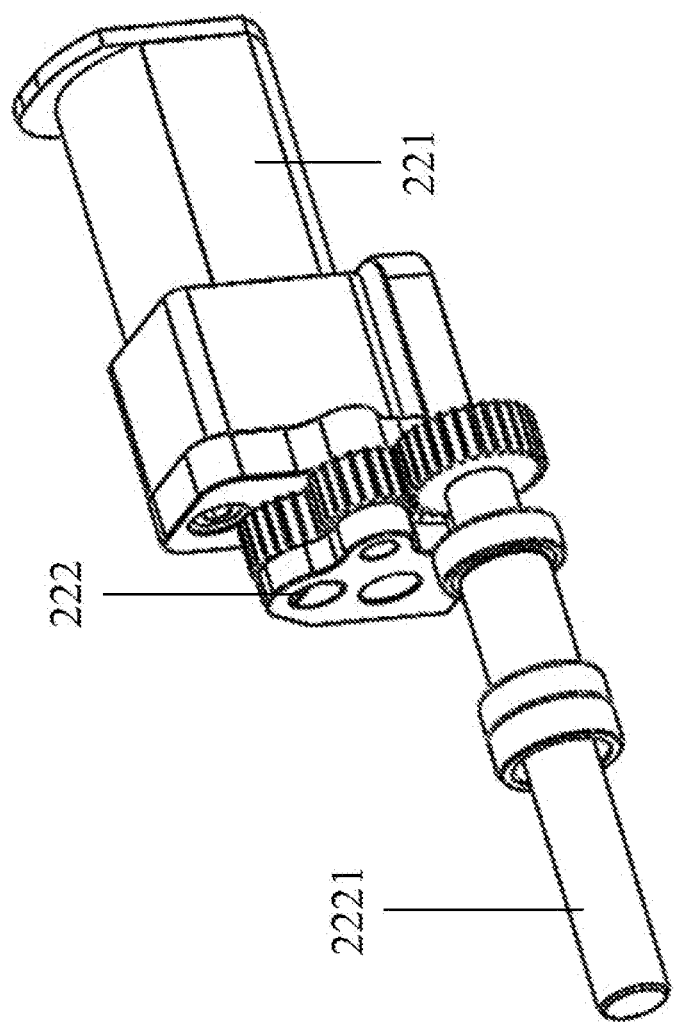
FIG. 5 schematically shows a three-dimensional composition diagram of a driving portion of a deflection detector from another perspective according to an embodiment of the present disclosure.

As shown in FIGS. 3 to 5, the output motor may output forward or reverse rotation actions according to the electrical signals for different motor rotation directions when controlled to rotate, so as to provide forward or reverse driving force, so that the interface portion performs forward or backward linear movement along the axial direction z relative to the supporting portion when receiving and converting the rotation action provided by the driving force.

The gear unit 222 and the motor unit 221 are provided on the supporting frame 101. The gear unit 222 is in transmission connection with the motor unit 221. Such transmission connection refers to that, the output shaft of the motor unit 221 serves as a fixed shaft of the transmission gear of the gear unit 222 to drive the transmission gear to rotate, thereby driving the other gears of the gear unit 222 to rotate, ultimately achieving the rotation of the output shaft 2221 of the gear unit 222. The output shaft 2221 of the gear unit 222 is rotated connected to the interface portion by penetrating the rotating head 102 provided on the supporting frame 101, so that when the output shaft 2221 rotates, the interface portion is driven to perform forward or backward linear movement along the axial direction z relative to the supporting portion.

As shown in FIGS. 1 to 8, according to an embodiment of the present disclosure, the interface portion includes an interface seat 301 and a transmitter 302.

The interface seat 301 is in transmission connection with the gear unit 222 of the motor component and used to convert the rotation action of the driving portion into the linear movement action along the axial direction.

The transmitter 302 has an end connected to the interface seat 301 and the other end connected to the operating end, and the transmitter is used to convert the linear movement action of the interface seat 301 into the deflection action of the operating end.

As shown in FIGS. 3 to 5, the output shaft 2221 of the gear unit 222 is rotationally connected to the fixed block 311 provided on the interface seat 301 by penetrating the rotating head 102 provided on the supporting frame 101. That is, the output shaft 2221 may rotate relative to the fixed block 311 along the shaft hole in the axial direction z. The outer surface of the output shaft 2221 is provided with threads, and the inner surface of the shaft hole of the fixed block 311 has matching threads, resulting in the relative rotation between the output shaft 2221 and the fixed block 311. When the interface seat 301 is limited and cannot rotate as a whole and the output shaft 2221 rotates in the shaft hole of the fixed block 311, the overall interface seat may perform the forward and backward linear movement along the axial direction z relative to the supporting frame 101. When the output shaft 2221 rotates in a forward direction, the interface seat performs the forward linear movement, expanding the distance between the interface seat 301 and the supporting frame 101. In contrast, when the output shaft 2221 rotates in reverse direction, the interface seat 301 performs the backward linear movement, reducing the distance between the interface seat 301 and the supporting frame 101, so as to achieve the conversion of the rotational output action of the motor component into the linear forward and backward movement action.

The interface seat 301 is actively connected to the transmitter 302. The transmitter 302 may be connected to the operating end through a deflection rod. During the forward and backward movement of the interface seat 301, the transmitter 302 transmits the action of the forward and backward movement to the operating end, so that the operating end converts the action of the forward and backward movement into a forward or reverse deflection action. The deflection angle of the deflection action is controlled according to the distance of the forward and backward movement.

As shown in FIGS. 1 to 8, according to an embodiment of the present disclosure, the detecting portion includes a thimble component 401 provided in a fixed hole g of the interface seat 301 and used to detect the movement position of the linear movement action of the interface portion along the axial direction relative to the supporting portion.

As shown in FIGS. 1 to 8, according to an embodiment of the present disclosure, the thimble component 401 includes a plurality of thimbles 411, a thimble sleeve 412, and a fixed sleeve 413.

The plurality of thimbles 411 are in contact with electrical contacts of the supporting portion, and different detection signals are formed in response to electrical contacts at different positions being detected, and the movement position is fed back using the detection signal.

The thimble sleeve 412 is sheathed the plurality of thimbles 411, and used to provide attachment positions for the plurality of thimbles 411.

The fixed sleeve 413 is sheathed the thimble sleeve 412, provided in the fixed hole g of the interface seat 301, matched with the fixed hole g, and used to fix the thimble sleeve 412 sheathed the plurality of thimbles 411 in the fixed hole g.

Figure 2:
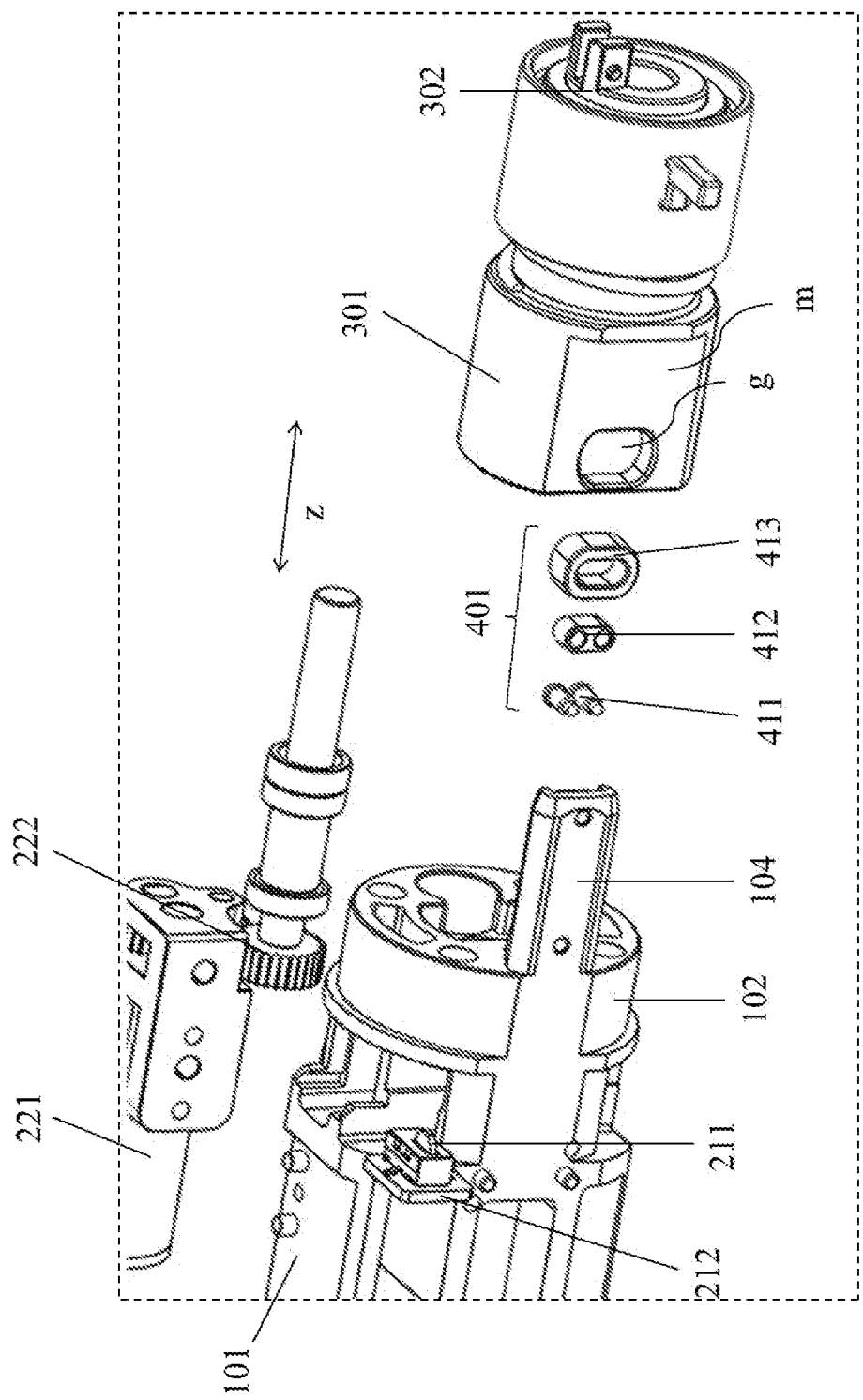
FIG. 2 schematically shows a three-dimensional explosion diagram of a part of a deflection detector from another perspective according to an embodiment of the present disclosure.

As shown in FIGS. 1 to 2, a smooth moving surface m is provided on a symmetrical ring surface of the interface seat 301 relative to the fixed block 311. The moving surface m is a plane. The plane is provided with the fixed hole g at an edge of the interface seat 301 facing the rotating head 102, so as to fix the thimble component 401 through the fixed hole and ensure that the thimble component 401 may perform a more accurate detection response to the distance of the forward and backward linear movement of the interface seat 301. The moving surface m may also be used for the rotation limit function of the interface seat 301, preventing the interface seat 301 from rotating with the rotation of the output shaft 2221 and ensuring that the interface seat 301 may generate relative linear movement.

The heads of the plurality of thimbles 411 of the thimble component 401 may protrude outward relative to the moving surface m. The thimble 411 may be a spring thimble. The number of thimbles 411 may be at least two, so that the structural stability of the thimble component 411 is improved while ensuring accurate detection, thereby extending the service life of the thimble component. Furthermore, the structure of the thimble component 401 is designed to be smaller, more stable and reliable, and have a longer lifespan, through the structure cooperation of the thimble sleeve 412 with the plurality of thimbles 411, as well as the structure cooperation of the fixed sleeve 413 with the thimble sleeve 412 having the plurality of thimbles 411 and the fixed hole g.

As shown in FIGS. 1 to 8, according to an embodiment of the present disclosure, the supporting portion further includes a limiting plate 104 provided on an edge of an end surface of the rotating head 102 facing the interface portion and corresponding to the fixed hole g of the interface seat 301.

A rear end electrical contact group, a zero position electrical contact group, and a front end electrical contact group are provided on a surface of the limiting plate 104 facing the interface seat 301, and movement position detections on a rear end position, a zero position, and a front end position of the interface portion relative to the supporting portion are achieved when the rear end electrical contact group, the zero position electrical contact group, and the front end electrical contact group are in contact with the plurality of thimbles 411 of the thimble component 401.

The inner surface of the limiting plate 104 corresponding to the moving surface m of the interface seat 301 may achieve relative movement and rotation limit between the limiting plate 104 and the interface seat 301. That is, after the interface seat 301 is driven by the rotation of the output shaft 2221 as described above, the limiting plate 104 fixed on the end surface of the rotating head 102 may limit the rotation of the interface seat 301 by cooperating with the moving surface m, so that the interface seat 301 may only move in a straight line along the axial direction z, achieving the linear movement of the interface seat 301 relative to the limiting plate 104.

A zero position electrical contact group is provided at the center position on the inner surface of the limiting plate 104, which has the same number of electrical contacts as the plurality of thimbles 411 of the thimble component 401. When the plurality of thimbles 411 of the thimble component 401 are in contact with the plurality of electrical contacts of the zero position electrical contact group one by one, the zero position electrical contact group may serve as a starting position of the interface seat 301 relative to the limiting plate 104. When the interface seat 301 moves forward towards the operating end relative to the limiting plate 104, the thimble component 401 leaves the starting position and approaches the front end electrical contact group. When the thimble component 401 is in contact with the plurality of electrical contacts of the front end electrical contact group one by one, the front end electrical contact group may be used as the front end limit of the interface seat 301 relative to the limiting plate 104, that is, the interface seat 301 cannot continue to move forward relative to the limiting plate 104, which adds the maximum forward deflection detection for the deflection operation. Correspondingly, when the thimble component 401 leaves the starting position, approaches the rear end electrical contact group, and is in contact with the plurality of electrical contacts of the rear end electrical contact group one by one, the rear end electrical contact group may be used as the rear end limit of the interface seat 301 relative to the limiting plate 104, that is, the interface seat 301 cannot continue to move backward relative to the limiting plate 104, which adds the maximum reverse deflection detection for the deflection operation.

The size of the limiting plate 104 may be 4 mm*17 mm, extending 16.5 mm forward from the bottom of the supporting frame 101. The bottom of the interface seat 301 is designed for cooperating the plane m with the inner surface of the limiting plate 104 to perform linear movement and rotation limit. In addition, the middle of the interface seat 301 may be hollowed out, which may be used to fix structures, such as a pin connection piece and a thimble shim, for outputting the thimble detection signal.

It should be noted that the electrical contacts of the limiting plate 104 have a certain width, so that the contact between the thimble 411 and the electrical contacts is maintained as an edge contact, thereby ensuring the accuracy of detection during movement and avoiding poor contact situations. Moreover, due to the left and right displacement deviation for the left and right deflection of the deflection detection contact, there is a forward and backward displacement deviation of the thimble 411 on the limiting plate 104, so that the actual contact position between the round head thimble 411 and the edge is not in the center of the limiting plate 104, causing the deflection detection contact to shift left and right (such as 4 mm to the left and 3 mm to the right). Therefore, the above shifting dimensions need to be taken into account to ensure equal travel on both sides.

Based on the deflection detector of embodiments of the present disclosure, the fully single handed operation on the medical device applying the deflection detector may be achieved, with clear steps and prompt information. Specifically, a plurality of deflection buttons with specific distribution designs may be provided on the handle, and when the left hand holds and operates the handle, the operating end deflects to the right when pressing an upper deflection button on the handle; and the operating end deflects to the left when pressing a lower deflection button on the handle; on the contrary, when the right hand holds and operates the handle, the operating end deflects to the left when pressing the upper deflection button on the handle; and the operating end deflects to the right when pressing the lower deflection button on the handle, which achieves single handed hold and control, fully in line with ergonomic design. The detecting portion of the present disclosure may actually be expanded to position detections at various angles, achieving various detection functions.

Figure 9:
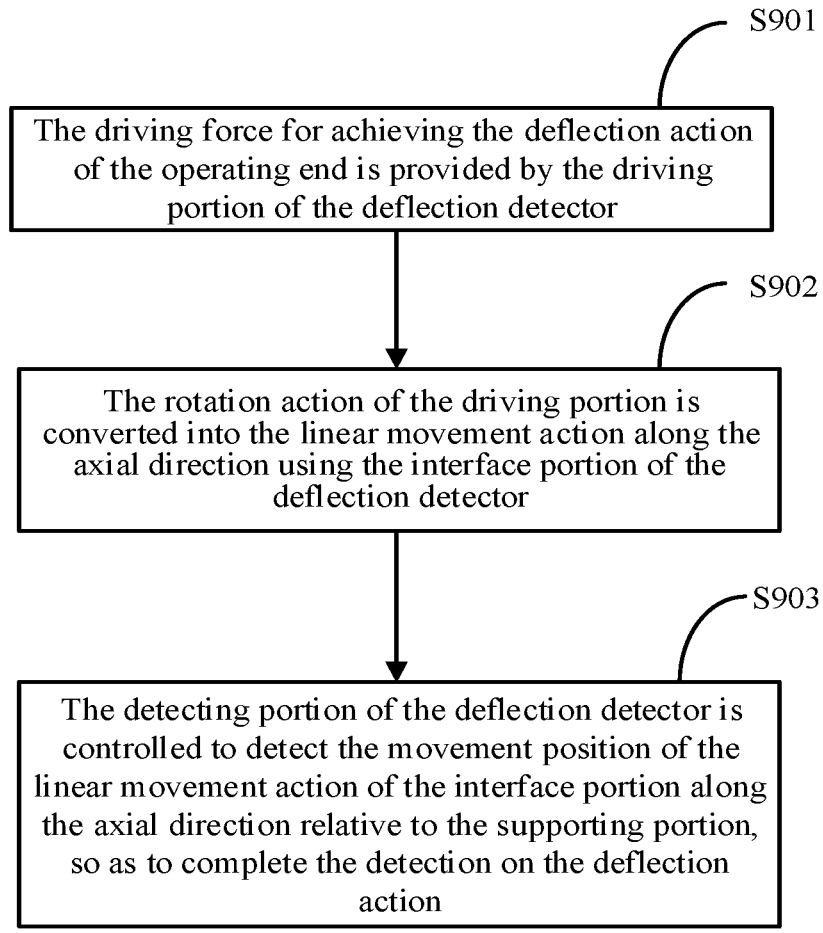
FIG. 9 schematically shows a flowchart of a method of controlling a deflection detector according to an embodiment of the present disclosure.

As shown in FIG. 9, another aspect of the present disclosure provides a method of controlling the above-described deflection detector, including: steps S901 to S903.

In the step S901, in response to a detection instruction, the driving force for achieving the deflection action of the operating end is provided by the driving portion of the deflection detector.

In the step S902, the rotation action of the driving portion is converted into the linear movement action along the axial direction using the interface portion of the deflection detector.

In the step S903, the detecting portion of the deflection detector is controlled to detect the movement position of the linear movement action of the interface portion along the axial direction relative to the supporting portion, so as to complete the detection on the deflection action.

The detection instruction may be a detection electrical signal generated by the user (such as a surgeon) manually triggering the switch button, for indicating the start of the deflection detection process.

To implement the control method shown in FIG. 9, an embodiment of the present disclosure provides a measurement and control system for implementing the control method.

Taking the new electric stapler and the jaw component provided in embodiments of the present disclosure as an example, the deflection control process of the method of controlling the deflection detector of the new electric stapler is further described in detail as follows.

By using the motor to control the left or right or up or down deflection of the anvil and the seat of the staple cartridge, and with a function of detecting the angle of the rotating head, the following may be achieved no matter what angle the rotating head is at: when the left hand holds and operates the handle, the jaw deflects to the right when pressing the upper deflection button on the handle; and the jaw deflects to the left when pressing the lower deflection button on the handle; when the right hand holds and operates the handle, the jaw deflects to the left when pressing the upper deflection button on the handle; and the jaw deflects to the right when pressing the lower deflection button on the handle, which is fully in line with ergonomic design.

In combination with the content shown in FIGS. 1 to 8, the process of the method of controlling the deflection detector for the new electric stapler is further explained as follows.

The deflection action of the new electric stapler is achieved through two steps. Firstly, the rotating housing 103 is manually rotated so that the anvil and the seat of the staple cartridge move in a circular motion at any angle. Then, the motor component is used to drive the anvil and the seat of staple cartridge to deflect to reach the surgical position. The new electric stapler has a function of detecting the rotation position.

The circuit board 212 for recognizing the rotation direction is fixedly installed on the supporting frame 101. The switching element 211 for detecting the rotation direction is provided on the circuit board 212. When the rotating housing 103 rotates, the rotating housing 103 is not in contact the switching element 211 within the range of 0° to 180°, and there is no signal output from the switching element 211. When the rotating housing 103 rotates within the range of 180° to 360°, the switching element 211 is triggered by the rotating housing 103 through the inclined surface, and the circuit board 212 is triggered by the switching element 211. A trigger signal is output through the circuit board 212 to complete the driving excitation function.

The motherboard receives the trigger signal to determine the rotation direction of the deflection motor of the motor component. The deflection motor drives the fixed block 311 to move forward and backward. The rotation of the fixed block 311 drives the transmitter 302 to move forward and backward. The transmitter 302 drives the deflection rod to move forward and backward. The deflection rod drives the middle deflection rod to move forward and backward. The middle deflection rod pulls the seat of the staple cartridge to rotate around the upper and lower fixing plates, completing the deflection action of the jaw component.

It may be seen that the above-described deflection detector of embodiments of the present disclosure adjusts the function of the left lower deflection button or the left upper deflection button through the motherboard, so as to achieve: when the left hand holds and operates, the jaw deflects to the right when pressing the upper deflection button; and the jaw deflects to the left when pressing the lower deflection button; when the right hand holds and operates, the jaw deflects to the left when pressing the upper deflection button; and the jaw deflects to the right when pressing the lower deflection button, which is fully in line with ergonomic design. It may be seen that the above structure may achieve fully single handed operation, with clear steps and prompt information. Since the device is safe and reliable, a closed-loop control system is adopts, the position detection is added, the deflection process is decomposed, and different software processes are used, the motor torque output is more reasonable and stable, effectively preventing accidental tissue damage and avoiding the risk of expanding the surgical range caused by clamping too thick tissue.

Figure 10:
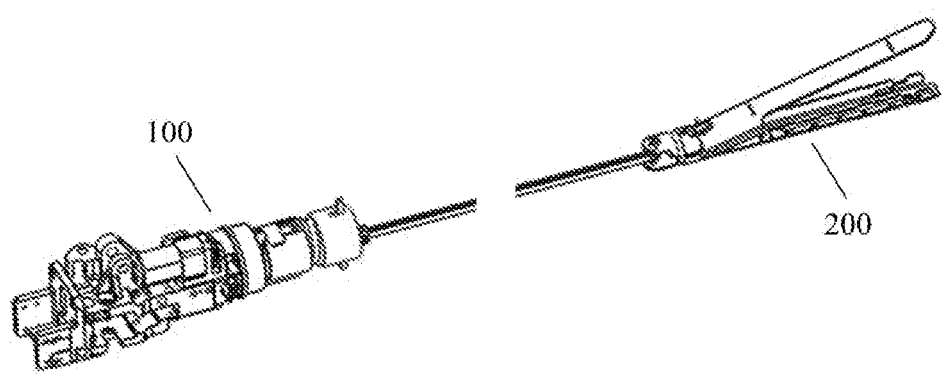
FIG. 10 schematically shows a three-dimensional composition diagram of a part of a structure of an electric stapler having the above-described deflection detector 100 according to an embodiment of the present disclosure.

As shown in FIG. 10, another aspect of the present disclosure provides an electric stapler, including the above-described deflection detector 100 and a jaw component 200.

The above-described deflection detector 100 is used to detect the movement position of the linear movement action of the interface portion along the axial direction relative to the supporting portion.

The jaw component 200 is in transmission connection with the interface portion of the deflection detector and serves as the operating end to perform the deflection action according to the detection on the movement position.

Specifically, the deflection detector and the control method in embodiments of the present disclosure may be referred to FIGS. 1 to 9 above, which will not be repeated here.

The deflection detector may be applied to a new type of electric endoscope linear cutting stapler for dissection, resection, and/or establishment of anastomosis, which is mainly suitable for operations of open or minimally invasive general surgery, obstetrics and gynecology, urology, thoracic surgery, and pediatric surgery. The deflection detector may be used in cooperation with anastomosis lines or tissue support materials, and may also be used for dissection and resection of liver parenchymal tissue (liver vascular system and biliary structure), pancreas, kidney, and spleen. The electric endoscope linear cutting stapler includes the body and component parts, and is a disposable product that may only be used in one surgery. Due to the disposable nature of the electric endoscope linear cutting stapler, cross infection during surgery is avoided.

Another aspect of the present disclosure provides a medical device, including the above-described deflection detector. Therefore, an electronic limit position detection may be added on the premise of having mechanical limits, so that the jaw component may stop deflecting before hitting the mechanical limit portion when performing the deflection operation, effectively preventing the deflection impact. In addition, the deflection process does not require manual force, the deflection direction is stable which is not limited by the position of the jaw, and continuous angle rotation may be achieved. The deflection direction and angle meet the doctor's expectations, and fully single handed operation may be achieved.

At this point, a detailed description of embodiments of the present disclosure has been provided in conjunction with the accompanying drawings.

The specific embodiments described above further elaborate on the purposes, technical solutions, and beneficial effects of the present disclosure. It should be understood that the above are only specific embodiments of the present disclosure and are not intended to limit the present disclosure. Any modifications, equivalent substitutions, improvements, etc. made within the spirit and principles of the present disclosure should be included in the scope of protection of the present disclosure.

What is claimed is:

1. A deflection detector, applied to a detection on a deflection action of an operating end of a medical device, comprising:
    a driving portion configured to perform a rotation action to provide a driving force for achieving the deflection action of the operating end;
    an interface portion in transmission connection with the driving portion and configured to convert the rotation action of the driving portion into a linear movement action along an axial direction; and
    a detecting portion provided on the interface portion and configured to detect a movement position of the linear movement action of the interface portion along the axial direction relative to a supporting portion, so as to complete the detection on the deflection action.

2. The deflection detector according to claim 1, further comprising:
    the supporting portion configured to support the deflection detector,
    wherein the driving portion is provided on the supporting portion.

3. The deflection detector according to claim 2, wherein the supporting portion comprises:
    a supporting frame being a frame structure with a hollow space and serving as a supporting main body of the supporting portion;
    a rotating head being a cylindrical structure, provided at an end of the supporting frame facing the operating end, and serving as a contact end between the supporting portion and the interface portion; and
    a rotating housing covering the rotating head and the interface portion and configured to rotate relative to the supporting frame, wherein an opening of the rotating housing is matched with an outer-ring surface of the cylindrical structure of the rotating head.

4. The deflection detector according to claim 3, wherein the driving portion comprises:

a switching component opposite to the rotating housing, provided on the supporting frame, and serving as a driving switch for the driving portion when the switching component is in contact with the rotating housing; and a motor component electrically connected to the switching component, provided in an accommodating space of the supporting frame, and configured to provide the driving force in response to a driving switch action of the switching component, so as to provide the rotation action to the interface portion.

5. The deflection detector according to claim 4, wherein the switching component comprises:

a switching element arranged opposite to the opening of the rotating housing and serving as a contact element of the driving switch; and a circuit board provided on a side of the switching element, embedded on the supporting frame, electrically connected to the motor component, and configured to generate an electrical signal for controlling a motor rotation direction of the motor component.

6. The deflection detector according to claim 5, wherein the rotating housing comprises:

a semi-ring convex portion provided on the rotating housing along an outer edge of the opening of the rotating housing and opposite to the switching element, wherein two end portions of the semi-ring convex portion have sloping surfaces, wherein when the rotating housing rotates relative to the supporting frame and the sloping surface of the end portion of the semi-ring convex portion is in contact with the switching element, the switching element triggers an electrical contact on the circuit board to generate the electrical signal for controlling the motor rotation direction of the motor component.

7. The deflection detector according to claim 5, wherein the motor component comprises:

a motor unit having an output motor and configured to control the output motor to rotate according to the electrical signal for the motor rotation direction, so as to provide the driving force; and a gear unit in transmission connection with the motor unit and configured to convert the driving force into the rotation action.

8. The deflection detector according to claim 4, wherein the interface portion comprises:

an interface seat in transmission connection with a gear unit of the motor component and configured to convert the rotation action of the driving portion into the linear movement action along the axial direction; and a transmitter having an end connected to the interface seat and the other end connected to the operating end, wherein the transmitter is configured to convert the linear movement action of the interface seat into the deflection action of the operating end.

9. The deflection detector according to claim 8, wherein the detecting portion comprises:

a thimble component provided in a fixed hole of the interface seat and configured to detect the movement position of the linear movement action of the interface portion along the axial direction relative to the supporting portion.

10. The deflection detector according to claim 9, wherein the thimble component comprises:

a plurality of thimbles in contact with electrical contacts of the supporting portion, wherein different detection signals are formed in response to electrical contacts at different positions being detected, and the movement position is fed back using the detection signal;

a thimble sleeve sheathed the plurality of thimbles, and configured to provide attachment positions for the plurality of thimbles; and a fixed sleeve sheathed the thimble sleeve, provided in the fixed hole of the interface seat, matched with the fixed hole, and configured to fix the thimble sleeve sheathed the plurality of thimbles in the fixed hole.

11. The deflection detector according to claim 10, wherein the supporting portion further comprises:

a limiting plate provided on an edge of an end surface of the rotating head facing the interface portion and corresponding to the fixed hole of the interface seat, wherein a rear end electrical contact group, a zero position electrical contact group, and a front end electrical contact group are provided on a surface of the limiting plate facing the interface seat, and movement position detections on a rear end position, a zero position, and a front end position of the interface portion relative to the supporting portion are achieved when the rear end electrical contact group, the zero position electrical contact group, and the front end electrical contact group are respectively in contact with the plurality of thimbles of the thimble component.

12. A method of controlling the deflection detector of claim 1, comprising:

providing, by the driving portion of the deflection detector, the driving force for achieving the deflection action of the operating end, in response to a detection instruction;

converting, using the interface portion of the deflection detector, the rotation action of the driving portion into the linear movement action along the axial direction; and controlling the detecting portion of the deflection detector to detect the movement position of the linear movement action of the interface portion along the axial direction relative to the supporting portion, so as to complete the detection on the deflection action.

13. An electric stapler, comprising:

the deflection detector of claim 1 configured to detect the movement position of the linear movement action of the interface portion along the axial direction relative to the supporting portion; and a jaw component in transmission connection with the interface portion of the deflection detector and serving as the operating end to perform the deflection action according to the detection on the movement position.

14. A medical device comprising the deflection detector of claim 1.

* * * * *